United States Patent [19]

Humbert et al.

[11] 3,991,178
[45] Nov. 9, 1976

[54] MENTHYL ESTER OF N-ACETYLGLYCINE AND ORAL COMPOSITIONS CONTAINING SAME

[75] Inventors: Françoise Humbert, Paris; Gerard Guth, Franconville; Yves Tollard d'Audiffret, Cabris, all of France

[73] Assignee: Lever Brothers Company, New York, N.Y.

[22] Filed: July 15, 1974

[21] Appl. No.: 488,856

[30] Foreign Application Priority Data

July 13, 1973 Luxembourg .......................... 68016

[52] U.S. Cl. ................................. 424/54; 424/48; 260/482 R
[51] Int. Cl.² ......................................... A61K 7/22
[58] Field of Search .................. 424/54; 260/482 R

[56] References Cited
UNITED STATES PATENTS 3,793,446   2/1974   Moeller et al. ........................ 424/48

OTHER PUBLICATIONS

*Chemical Abstracts*, vol. 67, entry 32923c, 1967.

*Primary Examiner*—Lewis Gotts
*Assistant Examiner*—Cary Owens
*Attorney, Agent, or Firm*—James J. Farrell; Melvin H. Kurtz; Kenneth F. Dusyn

[57] ABSTRACT

The menthyl ester of N-acetylglycine, which is prepared by esterification of glycine with menthol and acetylation, is used in compositions containing it and an orally-acceptable carrier, especially dentifrices, to give a refreshing effect in the mouth.

5 Claims, No Drawings

MENTHYL ESTER OF N-ACETYLGLYCINE AND ORAL COMPOSITIONS CONTAINING SAME

This invention relates to a menthyl ester, to processes for preparing it and compositions containing it.

Menthol produces a fresh or cool sensation by its effect on the nerve endings of the oral and nasal cavities and this refreshing effect is used by incorporating it in products for oral administraton. However, the use for this purpose of menthol, or products such as natural peppermint oils which contain it, is limited by the strength of the flavour and the burning sensation which they can produce.

It has now been found that the menthyl ester of N-acetylglycine produces a longer-lasting cool sensation and refreshing effect with less predominant flavour and burning sensation. Moreover the N-acetylglycine ester is much superior to other menthyl esters of closely related structure. Thus although some menthyl esters of amino-acids show the refreshing effect, they have in general an ammoniacal smell, and their salts, such as the hydrochloride, have an unpleasant taste. Esters of menthol with acetylated amino-acids other than glycine exhibit the refreshing effect but are unacceptably bitter. The following table gives the results of organoleptic tests carried out on some of these compounds for comparison: for the tests 10 drops of a 10% alcoholic solution of the compound were taken by mouth on a lump of sugar, and the duration of the refreshing and bitterness effects was measured.

| Compound | Freshness Effect | Duration Min. | Bitterness Effect | Duration Min. |
|---|---|---|---|---|
| Menthol | Immediate and strong | 15 | Strong | 1.5 |
| Menthyl esters of N-acetyl amino acids | | | | |
| Alanine | Immediate and strong | 16 | Very strong then suddenly vanishing | 5 |
| α-Amino-butyric acid | Immediate and moderate | 17 | Moderately strong | 5 |
| Leucine | Immediate and weak | 5 | Slight to moderate | 1 |
| Glycine | Faint at start, appearing in 2 minutes | 20 | Slight, increasing up to 1 minute, then quickly subsiding | 1 |

The invention accordingly provides the menthyl ester of N-acetyl glycine as a new compound that is useful in compositions for oral administration.

In a process of the invention, the menthyl ester of N-acetyl glycine is prepared by esterifying glycine with menthol and acetylating the glycine either before or after the esterification. The esterification and acetylation can be carried out by standard methods. Thus menthol and glycine can be heated together in the presence of an acid catalyst, for instance sulphuric or p-toluene sulphonic acid, preferably used in slight excess over that necessary to neutralise the amino group of the glycine, the resulting ester contacted with a base, for instance sodium carbonate, to liberate the amino group, and the menthyl ester of glycine obtained then acetylated with acetyl chloride or acetic anhydride. Preferably, however, the acetylation of the glycine is carried out first and the N-acetylglycine is then esterified by heating with menthol in the presence of the acid catalyst, as this gives a better yield of product. Accordingly the invention includes both a process in which the menthol ester of glycine is acetylated, and a process in which N-acetylglycine is esterified with menthol.

The compositions of the invention consist of the menthyl ester of N-acetyglycine and an orally-acceptable carrier. By carrier is meant the remainder of the composition, whether or not some or all of it has another function. The ester can be present in solution or suspension in, or adsorbed upon, or encapsulated in, the carrier or part of the carrier. Such compositions can be in solid, for instance powder or tablet, paste, or liquid form containing an amount of the ester effective to produce a refreshing sensation when introduced into the mouth by release of the ester from the composition. Thus the ester will be brought into contact with the surfaces of the oral cavity when a dental powder or toothpaste (dental cream) containing it is used in brushing the teeth, when a dental lozenge containing it is sucked, when a chewing gum containing it is chewed, and when a mouthwash containing it is used to rinse the mouth. An effective amount of the ester is in general from 0.025 to 2%, and preferably from 0.1 to 0.2% by weight of the composition is employed.

The composition can contain a sweetening agent, for example dextrose, laevulose, saccharin, sodium cyclamate or a dihydrochalcone, and from 0.01 to 5% of sweetening agent by weight of the composition will generally be present. The composition will usually contain a flavouring agent, for example an essential oil, in amount from 0.01 to 5% by weight of the composition.

Particularly important are dentifrices, in which the carrier includes a dental polishing agent. Suitable polishing agents are those abrasives commonly used in dentifrices, for example calcium carbonate, dicalcium orthophosphate, tricalcium orthophosphate, calcium pyrophosphate, insoluble sodium metaphosphate, hydrated alumina and silica, and particles of thermosetting resin, for instance urea-formaldehyde and melamine-formaldehyde resin. The amount of dental polishing agent will generally be from 5 to 99.5%, and preferably from 10 to 60%, by weight of the composition, depending on the form of the dentifrice. A dental powder will generally contain the polishing agent, a surface-active agent, a flavouring agent and a sweetening agent, whereas a toothpaste will generally contain in addition water, a humectant, a binder and a preservative. Preferably therefore a composition of the invention contains a dental polishing agent and a surface-active agent, for example sodium lauryl sulphate, sodium coconut monoglyceride sulphonate, sodium N-lauroyl sarcosinate, dioctyl sodium sulphosuccinate, sodium lauryl sulpho-acetate. Generally from 0.01 to 10% and preferably from 0.5 to 55 of surface-active agent by weight of the composition is present.

Suitable as humectants are glycerol, propylene glycol, sorbitol and polyethylene glycols. Examples of suitable binders are starch, gum karaya, gum tragacanth, sodium alginate, Irish moss extract, methylcellulose, and sodium carboxymethylcellulose. Sodium benzoate and methyl p-hyroxybenzoate are suitable preservatives. The amount of water, humectant and binder present will depend upon the consistency of paste composition desired, but will generally be such as to make the composition extrudable from an aerosol container or a collapsible tube. A toothpaste can, for example, contain from 10 to 30% of water and from 5 to 70% of humectant by weight. Usually from 0.1 to 10%, and preferably from 0.2 to 5% of binder is present by weight of the composition.

Other ingredients which can be included in a toothpaste are whiteners, for instance titanium dioxide, optical brighteners, bleaching agents, chloroform, urea, diammonium phosphate, film-forming substances, for example silicones, germicides, for example dichlorophene and hexachlorophene, chlorophyll derivatives, vitamins, antibiotic agents, enzymes, and astringents and colouring agents.

Compositions of the invention can also contain a cariostatic agent, for example sodium fluoride, stannous flouride, or sodium monofluorophosphate. From 0.01 to 1%, and preferably from 0.02 to 0.5%, of cariostatic agent can be used by weight of the composition. Other ingredients that can be employed in a dentifrice composition are described in Cosmetic Science and Technology, by Balsam and Sagarin, (Wiley-Interscience) Second Edition (1972).

The pH produced in the mouth by the composition should be within the range 4 to 8, and preferably from 4.5 to 6.5. Citric acid can be incorporated to provide a suitable pH.

A suitable base for a carrier for a mouthwash composition can be provided by aqueous ethanol. Typical ingredients of mouthwashes suitable as carriers for mouthwash compositions are described in the textbook referred to above.

Compositions of the invention can be prepared from the ingredients by standard methods in which the menthyl ester is incorporated in the orally-acceptable carrier, for instance those described in the above textbook.

The invention is illustrated by the following Examples.

EXAMPLE 1

A mixture of N-acetylglycine (obtained by the acetylation of glycine with acetic anhydride; 23.4g, 0.2 mol), menthol (48g), p-toluenesulphonic acid (5g), benzene (280 ml) and toluene (120 ml) was heated under reflux for 15 hours, with removal of the water produced on esterification. The cooled solution was filtered, washed with aqueous sodium bicarbonate solution, and with water until neutral. The solvent was removed by evaporation and the residual oil dissolved in hexane (65 ml) and cooled to 0°. Crystals of the menthyl ester of N-acetylglycine (35.5g) were desposited on standing. On recrystallisation from hexane the ester had mp 61°–62° C.

EXAMPLE 2

A mixture of glycine (15g, 0.2 mol), menthol (48g), p-toluenesulphonic acid (48g), benzene (280 ml) and toluene (120 ml) is heated under reflux until esterification is complete, the solvent evaporated off and the residue extracted with ether to give the aminoester tosylate, which is hydrolysed with sodium carbonate and the free amino-ester isolated and purified by distillation under reduced pressure. The amino-ester (0.9g), acetic anhydride (8.5 ml) and water (12.5 ml) are heated together under reflux for 10 minutes, the reaction product cooled, and the menthyl ester of N-acetylglycine recovered as in Example 1.

EXAMPLE 3

A toothpaste was prepared by conventional methods from the following ingredients in parts by weight.

| | |
|---|---|
| Menthyl ester of N-acetylglycine | 0.20 |
| Silica | 18 |
| Sodium lauryl sulphate | 1.5 |
| Glycerol | 58 |
| Sodium saccharinate | 0.15 |
| Flavouring agent | |
| Bulgarian mint oil | 0.32 |
| Arvensis mint oil | 0.34 |
| Aqueous 1% thymol solution | 0.02 |
| Menthol | 0.05 |
| Natural anethole | 0.04 |
| Oil of wintergreen | 0.01 |
| Oil of cloves | 0.002 |
| Vanilla tincture | 0.017 |
| Ceylon cinnamon oil | 0.001 |
| Water | 21.35 |

On brushing the teeth with the paste a minty-wintergreen flavour was experienced with a fresh sensation persisting longer than when a similar paste without the menthyl ester was used.

EXAMPLE 4

A toothpaste was prepared by conventional methods from the following ingredients, in parts by weight.

| | |
|---|---|
| Menthyl ester of N-acetylglycine | 0.40 |
| Aluminium hydroxide | 42.50 |
| Alumina | 2.00 |
| Sodium lauryl sulphoacetate | 1.00 |
| Glycerol | 28.00 |
| Gum tragacanth | 0.50 |
| Sodium saccharinate | 0.05 |
| Methyl p-hydroxybenzoate | 0.10 |
| Flavouring agent | |
| Natural anethole | 0.25 |
| Synthetic anethole | 0.25 |
| Ceylon cinnamon oil | 0.10 |
| Oil of cloves | 0.05 |
| Coriander oil | 0.2 |
| Liquorice | 0.25 |
| Sweet fennel | 0.15 |
| Bitter fennel | 0.15 |
| Tarragon | 0.05 |
| Lemon oil | 0.05 |
| Water | 23.95 |

When the paste was used for brushing the teeth, an aniseed flavour with no menthol smell and a freshening effect subsisting for 40 minutes was experienced, whereas when a corresponding composition was used, in which the menthyl ester was replaced by a molecular equivalent quantity of Brazil menthol (0.245) and alcohol (0.155), an aniseed flavour with a predominating smell of mint and a freshening effect remaining for 25 minutes was experienced.

EXAMPLE 5

A mouthwash composition is prepared by mixing the following ingredients in parts by weight.

| | |
|---|---|
| Menthyl ester of N-acetylglycine | 0.8 |
| 95% Ethanol | 25 |
| Glycerol | 12 |
| Sodium saccharinate | 0.05 |
| Lemon oil | 0.4 |
| Polyoxyethylene (20) sorbitan monolaurate | 7 |

-continued

| Water | 54.75 |

Before use this mouthwash is diluted with an equal volume of water.

What is claimed is:

1. The menthyl ester of N-acetylglycine.
2. A composition comprising the menthyl ester of N-acetyl glycine in an amount effective to produce a fresh oral sensation and an orally acceptable carrier.
3. A method for producing a fresh sensation in oral compositions comprising incorporating the menthyl ester of N-acetyl glycine into said compositions in an amount effective to result in said fresh sensation.
4. A dentifrice composition comprising from 5 to 99.5% of a dental polishing agent, from 0.01 to 10% of a surface active agent, and from 0.025 to 2% of the menthyl ester of N-acetyl glycine, by weight of the composition.
5. A composition according to claim 4 containing from 0.01 to 5% of a sweetening agent by weight of the composition.

* * * * *